United States Patent
Clark et al.

(10) Patent No.: US 11,477,416 B2
(45) Date of Patent: Oct. 18, 2022

(54) PATIENT VIDEO MONITORING SYSTEMS AND METHODS HAVING DETECTION ALGORITHM RECOVERY FROM CHANGES IN ILLUMINATION

(71) Applicant: CareView Communications, Inc., Lewisville, TX (US)

(72) Inventors: Matthew Cameron Clark, Frisco, TX (US); Derek del Carpio, Corinth, TX (US)

(73) Assignee: Care View Communications, Inc., Lewisville, TX (US)

( * ) Notice: Subject to any disclaimer, the term of this patent is extended or adjusted under 35 U.S.C. 154(b) by 0 days.

(21) Appl. No.: 17/246,984

(22) Filed: May 3, 2021

(65) Prior Publication Data
US 2021/0258545 A1    Aug. 19, 2021

Related U.S. Application Data

(63) Continuation of application No. 16/836,094, filed on Mar. 31, 2020, now Pat. No. 11,032,522, which is a
(Continued)

(51) Int. Cl.
*G06T 7/11* (2017.01)
*H04N 7/18* (2006.01)
(Continued)

(52) U.S. Cl.
CPC ........... *H04N 7/183* (2013.01); *A61B 5/1128* (2013.01); *A61B 5/7207* (2013.01);
(Continued)

(58) Field of Classification Search
CPC ............ H04N 7/183; H04N 21/44218; H04N 5/2351; A61B 5/1128; A61B 5/7207;
(Continued)

(56) References Cited

U.S. PATENT DOCUMENTS

| 4,608,559 A | 8/1986 | Friedman et al. |
| RE32,327 E | 1/1987 | Biba et al. |

(Continued)

FOREIGN PATENT DOCUMENTS

| WO | WO200018054 A2 | 3/2000 |
| WO | WO2002063880 A1 | 8/2002 |

OTHER PUBLICATIONS

AHCPR. (May 1992). Panel for the Prediction and Prevention of Pressure Ulcers in Adults. Pressure Ulcers in Adults: Prediction and Prevention. Clinical Practice Guideline, No. 3. AHCPR Publication No. 92-0047. Rockville, MD: Agency for Health Care Policy and Research, Public Health Service, U.S. Department of Health and Human Services (http://www.ncbi.nlm.nih.gov/bookshelf/br.fcgi?book=hsahcpr&part=A4409).

(Continued)

*Primary Examiner* — Patrick E Demosky
(74) *Attorney, Agent, or Firm* — Meister Seelig & Fein LLP

(57) ABSTRACT

Various embodiments concern video patient monitoring with detection zones. Various embodiments can comprise a camera, a user interface, and a computing system. The computing system can be configured to perform various steps based on reception of a frame from the camera, including: calculate a background luminance of the frame; monitor for a luminance change of a zone as compared to one or more previous frames, the luminance change indicative of patient motion in the zone; and compare the background luminance to an aggregate background luminance, the aggregate background luminance based on the plurality of frames. If the background luminance changed by more than a predetermined amount, then the aggregate background luminance can be set to the background luminance, luminance infor- (Continued)

mation of the previous frames can be disregarded, and motion detection can be disregarded.

20 Claims, 6 Drawing Sheets

Related U.S. Application Data continuation of application No. 14/158,016, filed on Jan. 17, 2014, now Pat. No. 10,645,346.

(60) Provisional application No. 61/753,991, filed on Jan. 18, 2013.

(51) Int. Cl.
  *G08B 21/04* (2006.01)
  *A61B 5/00* (2006.01)
  *A61B 5/11* (2006.01)
  *H04N 21/442* (2011.01)
  *G08B 13/196* (2006.01)

(52) U.S. Cl.
  CPC ..... *G08B 21/0461* (2013.01); *G08B 21/0476* (2013.01); *A61B 5/0046* (2013.01); *A61B 5/7465* (2013.01); *A61B 2505/03* (2013.01); *A61B 2560/0242* (2013.01); *G08B 13/19604* (2013.01); *H04N 21/44218* (2013.01)

(58) Field of Classification Search
  CPC . A61B 5/0046; A61B 5/7465; A61B 2505/03; A61B 2560/0242; G08B 21/0461; G08B 21/0476; G08B 13/19604; G06T 2207/30232; G06T 7/20; G06T 7/11
  See application file for complete search history.

(56) References Cited

U.S. PATENT DOCUMENTS

| | | |
|---|---|---|
| 4,885,795 A | 12/1989 | Bunting et al. |
| 5,343,240 A | 8/1994 | Yu |
| 5,574,964 A | 11/1996 | Hamlin |
| 5,798,798 A | 8/1998 | Rector et al. |
| 5,995,146 A | 11/1999 | Rasmussen |
| 6,049,281 A | 4/2000 | Osterweil |
| 6,195,797 B1 | 2/2001 | Williams, Jr. |
| 6,259,443 B1 | 7/2001 | Williams, Jr. |
| 6,310,915 B1 | 10/2001 | Wells |
| 6,311,268 B1 | 10/2001 | Chu |
| 6,317,885 B1 | 11/2001 | Fries |
| 6,319,201 B1 | 11/2001 | Wilk |
| 6,323,896 B1 | 11/2001 | Dahmani et al. |
| 6,323,897 B1 | 11/2001 | Kogane |
| 6,429,233 B1 | 8/2002 | Oguri et al. |
| 6,456,320 B2 | 9/2002 | Kuwano et al. |
| 6,457,057 B1 | 9/2002 | Kageyu et al. |
| 6,529,233 B1 | 3/2003 | Allen |
| 6,544,200 B1 * | 4/2003 | Smith ............... A61B 5/6892 600/595 |
| 6,567,682 B1 | 5/2003 | Osterweil et al. |
| 6,594,837 B2 | 7/2003 | Khait |
| 6,646,556 B1 | 11/2003 | Smith et al. |
| 6,678,413 B1 | 1/2004 | Liang et al. |
| 6,757,909 B1 | 6/2004 | Maruo et al. |
| 6,803,945 B1 | 10/2004 | Needham |
| 6,856,249 B2 | 2/2005 | Strubbe et al. |
| 6,897,781 B2 | 5/2005 | Cooper et al. |
| 7,030,764 B2 | 4/2006 | Smith et al. |
| 7,078,676 B2 | 7/2006 | Smith et al. |
| 7,110,569 B2 | 9/2006 | Brodsky et al. |
| 7,378,975 B1 | 5/2008 | Smith et al. |
| 7,396,331 B2 | 7/2008 | Mack et al. |
| 7,405,770 B1 | 7/2008 | Gudmunson |
| 7,459,661 B2 | 12/2008 | Huber |
| 7,477,285 B1 | 1/2009 | Johnson |
| 7,567,688 B2 | 7/2009 | Nagaoka |
| 7,623,152 B1 | 11/2009 | Kaplinsky |
| 7,742,108 B2 | 6/2010 | Sheraizin |
| 7,761,310 B2 | 7/2010 | Rodgers |
| 7,801,328 B2 | 9/2010 | Au et al. |
| 7,830,962 B1 | 11/2010 | Fernandez et al. |
| 7,859,564 B2 | 12/2010 | Kelly, III et al. |
| 8,172,777 B2 | 5/2012 | Goto |
| 8,233,062 B2 | 7/2012 | Mitsuya |
| 8,243,156 B2 | 8/2012 | Sako |
| 8,311,282 B2 | 11/2012 | Luo |
| 8,471,899 B2 | 6/2013 | Johnson |
| 8,675,059 B2 | 3/2014 | Johnson et al. |
| 8,676,603 B2 | 3/2014 | Johnson |
| 8,687,918 B2 | 4/2014 | Tamura |
| 8,922,707 B2 * | 12/2014 | Kulkarni ............ H04N 5/23212 348/352 |
| 9,189,706 B1 | 11/2015 | Lee |
| 2001/0004400 A1 | 6/2001 | Aoki |
| 2002/0019984 A1 | 2/2002 | Rakib |
| 2002/0023297 A1 | 2/2002 | Khait |
| 2002/0044059 A1 | 4/2002 | Reeder et al. |
| 2002/0069417 A1 | 6/2002 | Kiger et al. |
| 2002/0104098 A1 | 8/2002 | Zustak et al. |
| 2002/0147982 A1 | 10/2002 | Naidoo et al. |
| 2002/0163577 A1 | 11/2002 | Myers |
| 2003/0010345 A1 | 1/2003 | Koblasz et al. |
| 2003/0025599 A1 | 2/2003 | Monroe |
| 2003/0181830 A1 | 9/2003 | Guimond et al. |
| 2004/0047419 A1 | 3/2004 | Wakabayashi |
| 2004/0075738 A1 | 4/2004 | Burke et al. |
| 2004/0077975 A1 | 4/2004 | Zimmerman |
| 2004/0105006 A1 | 6/2004 | Lazo et al. |
| 2004/0189475 A1 | 9/2004 | Cooper et al. |
| 2006/0024020 A1 | 2/2006 | Badawy |
| 2006/0098865 A1 | 5/2006 | Yang et al. |
| 2006/0239645 A1 | 10/2006 | Curtner et al. |
| 2006/0243798 A1 | 11/2006 | Kundu et al. |
| 2006/0244866 A1 | 11/2006 | Kishida |
| 2007/0132597 A1 * | 6/2007 | Rodgers ............... G06Q 10/10 348/E7.078 |
| 2007/0136102 A1 | 6/2007 | Rodgers |
| 2007/0147690 A1 | 6/2007 | Ishiwata |
| 2007/0160293 A1 | 7/2007 | Ishikawa et al. |
| 2008/0021731 A1 | 1/2008 | Rodgers |
| 2008/0123987 A1 | 5/2008 | Shen |
| 2008/0130961 A1 | 6/2008 | Kinoshita |
| 2008/0193020 A1 | 8/2008 | Sibiryakov et al. |
| 2009/0022398 A1 | 1/2009 | Ishikawa et al. |
| 2009/0070939 A1 | 3/2009 | Hann |
| 2009/0072142 A1 | 3/2009 | Blitzer |
| 2009/0119843 A1 | 5/2009 | Rodgers et al. |
| 2009/0185743 A1 | 7/2009 | Qi |
| 2009/0278934 A1 * | 11/2009 | Ecker ................. G06V 40/25 348/152 |
| 2009/0324023 A1 | 12/2009 | Tian et al. |
| 2010/0052904 A1 | 3/2010 | Noguchi |
| 2010/0134609 A1 | 6/2010 | Johnson |
| 2010/0166324 A1 | 7/2010 | Kundu et al. |
| 2010/0201849 A1 | 8/2010 | Cheng |
| 2010/0290698 A1 | 11/2010 | Freedman et al. |
| 2010/0296698 A1 | 11/2010 | Lien |
| 2012/0026308 A1 | 2/2012 | Ohnson et al. |
| 2013/0290015 A1 | 10/2013 | Johnson |
| 2014/0092247 A1 | 4/2014 | Clark et al. |
| 2014/0168397 A1 | 6/2014 | Greco et al. |
| 2014/0247334 A1 | 9/2014 | Johnson et al. |
| 2014/0267625 A1 | 9/2014 | Clark et al. |
| 2014/0288968 A1 | 9/2014 | Johnson |
| 2014/0313340 A1 | 10/2014 | Ecker et al. |

OTHER PUBLICATIONS

Chia-Feng Juang, Chia-Ming Chang, Jiuh-Rou Wu, and Demei Lee, Computer Vision-Based Human Body Segmentation and Posture

(56) References Cited

OTHER PUBLICATIONS

Estimation, Jan. 2009, IEEE Transactions on Systems, Man and Cybernetics—Part A: Systems and Humans, vol. 39, pp. 119-133.

* cited by examiner

PATIENT VIDEO MONITORING SYSTEMS AND METHODS HAVING DETECTION ALGORITHM RECOVERY FROM CHANGES IN ILLUMINATION

CROSS REFERENCE TO RELATED APPLICATION

This application claims the benefit of priority of U.S. Provisional Patent Application No. 61/753,991, filed Jan. 18, 2013, which is incorporated herein by reference in its entirety.

FIELD OF INVENTION

The present disclosure relates generally to systems and methods for patient monitoring by analyzing video frames to detect patient events. More particularly, the present disclosure relates to detection algorithms that can recover from unpredictable changes in illumination of the patient area being monitored while avoiding false alarms and improving detection of particular situations.

BACKGROUND

Healthcare facilities rely on patient monitoring to supplement interventions and reduce the instances of patient falls. Constant eyes-on monitoring of patients can be difficult for healthcare professionals to maintain. Video monitoring can be used to automate patient monitoring and increase the ability of a healthcare professional to effectively monitor a group of patients distributed between different rooms. Various systems and methods for patient video monitoring have been disclosed, such as U.S. Patent Application No. 2009/0278934 entitled System and Method for Predicting Patient Falls, U.S. Patent Application No. 2010/0134609 entitled System and Method for Documenting Patient Procedures; U.S. Patent Application No. 2012/0026308 entitled System and Method for Using a Video Monitoring System to Prevent and Manage Decubitus Ulcers in Patients, and U.S. Provisional Patent Application No. 61/707,227 entitled System and Method for Monitoring a Fall State of a Patient and Minimizing False Alarms.

Various routines can be run to analyze the output of a camera and identify events. An alert can be issued to summon a healthcare professional to intervene when events are detected. Such an automated system may be susceptible to light noise and other factors that can cause false alarms, which can burden a staff of healthcare professionals with unnecessary interventions. Video monitoring can rely on lighting of various kinds to allow visualization of the patient area and identify particular situations of interest. However, unpredictable changes in lighting of the patient's room can cause erroneous detections of situations warranting intervention and thereby causing false alarms. There exists a need for systems and methods for accounting for unpredictable changes in lighting to reduce the incidence of erroneous detections and false alarms.

SUMMARY

Various embodiments concern a system for monitoring a patient in a patient area having one or more detection zones. The system can comprise a camera, a user interface, and a computing system configured to receive a chronological series of frames from the camera. The computing system can further be configured to perform the following steps based on the reception of each frame of the chronological series: calculate a background luminance of the frame; calculate an aggregate background luminance based on a respective background luminance for each a plurality of previous frames of the chronological series; and for each of one or more zones, calculate a zone luminance based at least in part on the background luminance and a plurality of luminance values of a plurality of pixels of the zone. For each of one or more zones, the computing system can further be configured to detect patient motion based on a change between the zone luminance and a previous zone luminance of a previous frame exceeding a zone threshold. The computing system can further be configured to compare the background luminance of the frame to an aggregate background luminance and, if the background luminance changed relative to the aggregate background luminance by more than a threshold amount, disregard luminance information from the plurality of previous frames when performing the detecting patient motion step and the calculating the aggregate background luminance step for subsequent frames of the chronological series. If patient motion is detected, the computing system can generate an alert with the user interface if the background luminance changed relative to the aggregate background luminance by less than the threshold amount but refrain from generating the alert if the background luminance changed relative to the aggregate background luminance by more than the threshold amount.

The computing system can be configured to calculate the background luminance of the frame by determining an average pixel luminance based on each pixel of the frame. The computing system can configured to calculate the aggregate background luminance by averaging the respective background luminance for each the plurality of previous frames of the chronological series. The computing system can configured to calculate the aggregate background luminance based on the background luminance of the frame and the respective background luminance for each the plurality of previous frames of the chronological series.

In various embodiments, a computing system of a monitoring system can be configured to calculate a background luminance of a frame, and for each zone of one or more zones of the frame, monitor for a luminance change of the zone as compared to one or more frames of a plurality of frames that were previously received from the camera, the luminance change indicative of patient motion in the zone. The computing system can further be configured to compare the background luminance of the frame to an aggregate background luminance, the aggregate background luminance based on the plurality of frames, and if the comparison determines that the background luminance changed relative to the aggregate background luminance by more than a threshold amount, set the aggregate background luminance to the background luminance of the frame and disregard luminance of the plurality of frames in subsequent monitoring for the luminance change in the one or more zones.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
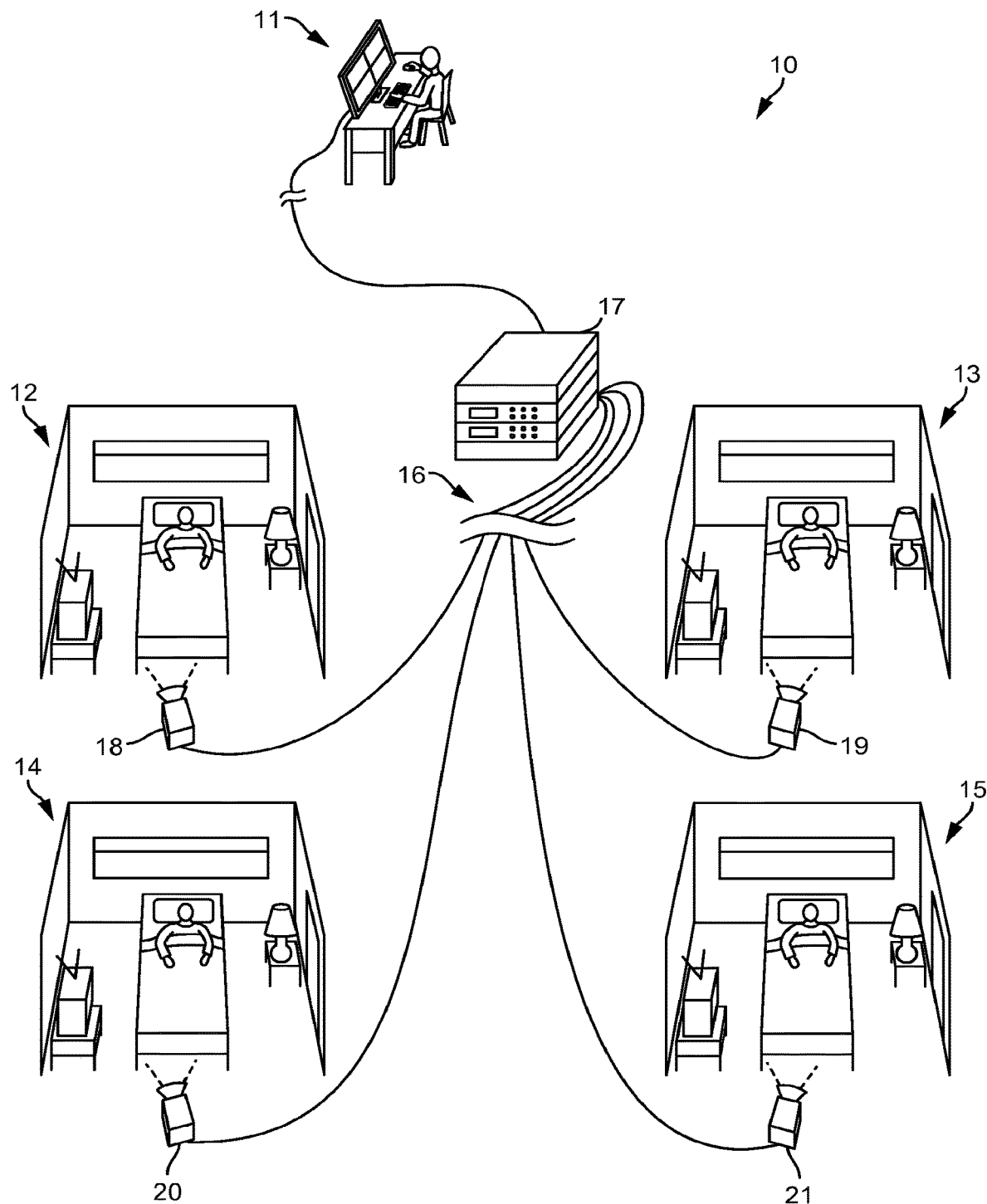
FIG. 1 is a schematic illustration of a monitoring system.

While the subject matter of the present disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present disclosure concern video monitoring to detect patient events. Such events can concern situations in which a patient is at increased risk or otherwise is in need of intervention. Patient events can include a patient at risk of falling, a patient falling, a patient outside of a designated area, and patient motion, among various other events.

FIG. 1 is a schematic diagram of a patient monitoring system 10. The patient monitoring system 10 can allow a healthcare professional to monitor multiple patient areas 12-15 from a monitoring station 11 via a computing system 17. The monitoring station 11 can comprise a user interface, which can include a screen and an input. The screen can display images of the patient areas 12-15, indications of one or more states of the patients being monitored, patient data, and/or other information. In some embodiments, the components of the monitoring station 11 are portable such that the monitoring station 11 can move with the healthcare processional.

While four patient areas 12-15 are shown in FIG. 1, any number of patient areas can be monitored at the monitoring station 11 via the computing system 17. The monitoring station 11 can be remote from the patient areas 12-15. For example, the monitoring station 11 can be on the same or different floor as the patient area 12-15, in the same or different building as the patient area 12-15, or located in a geographically different location as the patient area 12-15. Furthermore, the patient areas 12-15 can be remote from each other. The computing system 17 can be in one particular location or the components of the computing system 17 can be distributed amongst multiple locations. The computing system 17 can be at the monitoring station 11 or can be remote from the monitoring station 11 and/or the patient areas 12-15.

As shown in FIG. 1, a plurality of cameras 18-21 can be respectively positioned to view and generate frames of the plurality of patient areas 12-15. Information concerning the frames, such as analog or digital encodings of the frames, can be transmitted from the plurality of cameras 18-21 along data channels 16 to the computing system 17. In some cases, the computing system 17 is a single unit, such as a server or a personal computer (e.g., a desktop computer or a laptop computer). In some cases, the computing system 17 is distributed amongst several units, such as one or more personal computers, one or more servers, circuitry within one or more of the cameras 18-21, and/or other computing devices. In some cases, the computing system 17 is part of a cloud computing network. The data channels 16 can be wired lines of a network (e.g., a local area network) and/or wireless channels (e.g., Wi-Fi or cellular network).

Each of the plurality of cameras 18-21 can generate a chronological series of frames (e.g., as images). The plurality of cameras 18-21 can be analog or digital cameras. Each of the plurality of cameras 18-21 can capture a sequence of frames at a predetermined frame rate, such as six, eight, sixteen, twenty-four, or some other number of frames per second. The resolution of digital cameras is usually defined by the number of pixels both horizontally and vertically (such as 640×480) or as a total number of pixels in the image (such as 1.4 mega pixels), while the resolution of analog video cameras is typically defined by the number of television lines. Analog frames can be converted to digital frames by analog-to-digital conversion circuitry (e.g., as part of the computing system 17 and/or the plurality of cameras 18-21). The plurality of cameras 18-21 can have infrared illumination or night vision capabilities for operating in low light conditions.

Figure 2:
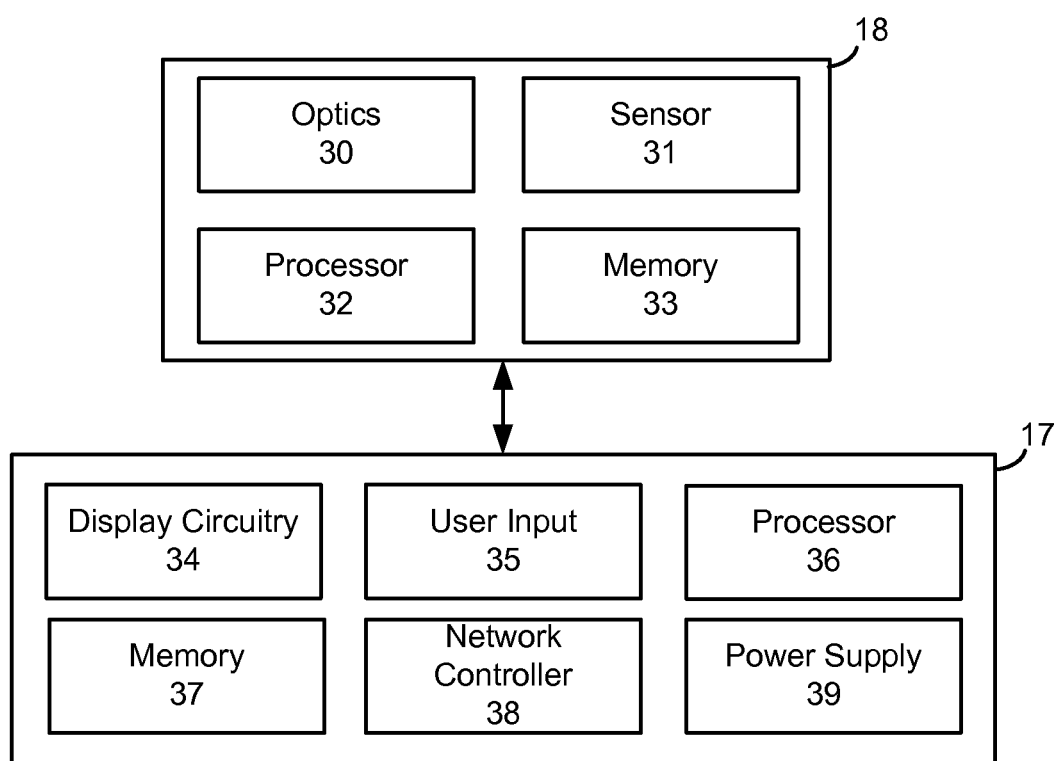
FIG. 2 is a block diagram of components of a monitoring system.

FIG. 2 shows a block diagram of circuitry of the monitoring system 10. Although camera 18 is specifically shown as an exemplar, the components of the camera 18 can be included as part of each camera and the monitoring system 10. The camera 18 can include optics 30. Optics 30 can include a lens, a filter, and/or other components for capturing and conditioning the light of the patient area. The camera 18 can further include a sensor 31 for converting light from the optics 30 into electronic signals. Different types of sensors 31 can be used depending on whether the camera 18 is analog (e.g., generating analog video) or digital (e.g., generating discrete digital frames). The sensor 31 can include a charge-coupled device (CCD) or a complementary metal-oxide-semiconductor (CMOS).

The camera 18 can further include a processor 32 and memory 33. The processor 32 can perform various computing functions, such as those described herein or otherwise useful for operating the camera 18. The memory 33 can be a non-transient computer readable storage medium (e.g., random access memory or flash) for storing program instructions and/or frames. For example, the processor 32 can be configured to execute program instructions stored on the memory 33 for controlling the camera 18 in converting light from the patient area 12 into digital signals with the sensor 31, storing the digital signals on the memory 33 as frame data, transferring the frame data to the computing system 17, and/or performing any other function. The processor 32 may perform various signal conditioning and/or image processing on the frames. The processor 32 may include a dedicated video processor for image processing. Although not illustrated, the camera 18 can further include a network interface controller and a power supply. The camera 18 may include a user interface which can include user controls and/or an audible alarm.

The computing system 17 can comprise a single housing or multiple housings among which circuitry can be distributed. The computing system 17 can include display circuitry 34 which can provide a graphics output to a screen. Display circuitry 34 can include a graphics processor and graphics memory which can support user interface functionality. Display circuitry 34 may be part of a separate display, such as a screen, handheld device, or remote terminal. Display circuitry 34 can facilitate the display of frames taken by the camera 18 of the patient area 12 on a screen and/or patient status information. User input circuitry 35 can include components for accepting user commands such as a keyboard, mouse, trackball, touchpad, touch screen, joystick, slider bar, or any other control. User input circuitry 35 can facilitate the definition of boundaries and monitoring zones, as will be further described herein.

The computing system 17 can include a processor 36 and memory 37. The memory 37 can be one or more discrete non-transient computer readable storage medium components (e.g., RAM, ROM, NVRAM, EEPROM, and/or FLASH memory) for storing program instructions and/or data. The processor 36 can be configured to execute program instructions stored on the memory 37 to control in the computing system 17 in carrying out the functions referenced herein. The processor 36 can comprise multiple discrete processing components to carry out the functions described herein as the processor 36 is not limited to a single processing component. The computing system 17 can include a network controller 38 for facilitating communication with the cameras 18-21 and/or other remote components. The computing system 17 can include a power supply 39 which can facilitate a connection to an electrical outlet and/or the power supply 39 can comprise a battery. Whether distributed or unified, the components of the computing system 17 can be electrically connected to coordinate and share resources to carry out functions.

Figure 3:
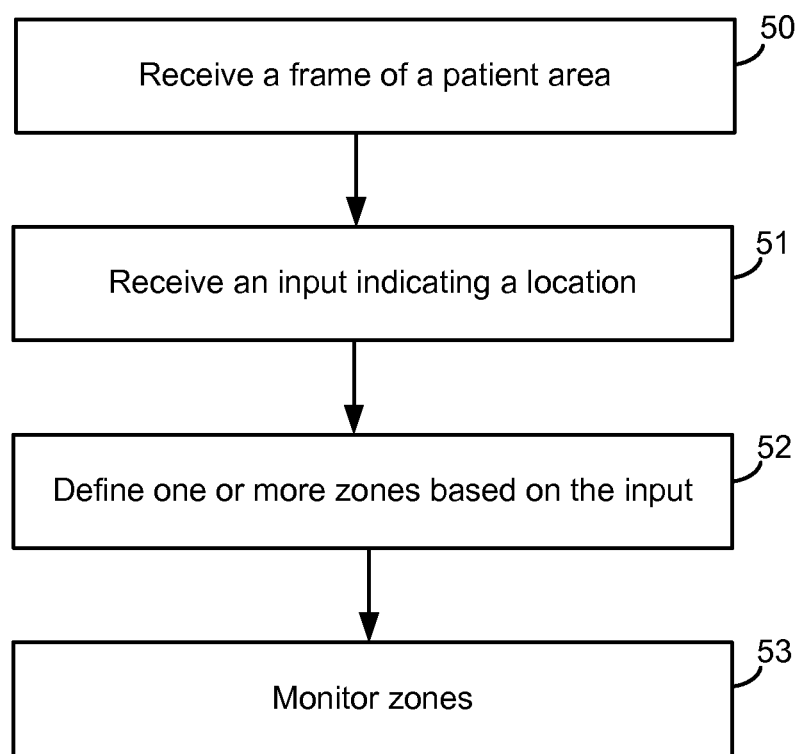
FIG. 3 is a flowchart of a method for initializing a monitoring system.

FIG. 3 illustrates a flow chart of a method for setting up a monitoring system to monitor a patient. The method includes receiving 50 a frame of a patient area. The frame can be an image generated by the camera 18 and can be received 50 by the computing system 17 of FIGS. 1-2. The frame can be displayed on a screen at the monitoring station 11. The patient area can correspond to any area associated with a patient and/or where increased risks to the patient are anticipated. Such areas can include a bed, a chair, a wheelchair, a tub, a shower, and/or an entryway.

The method can further include receiving 51 an input indicating a location. The input may be provided by a healthcare professional at the monitoring station 11 with a user interface. The indicated location can correspond to an area occupied by the patient and/or a risk to the patient. In some cases, a healthcare professional can indicate one or more boundaries associated with heightened fall risk, such as the left and right sides of a bed. For example, the healthcare professional can designate the left side and the right side of the bed 60 shown in FIG. 4. It is noted that patient areas may be automatically identified through a pattern recognition procedure implemented in the monitoring system in some embodiments.

Figure 4:
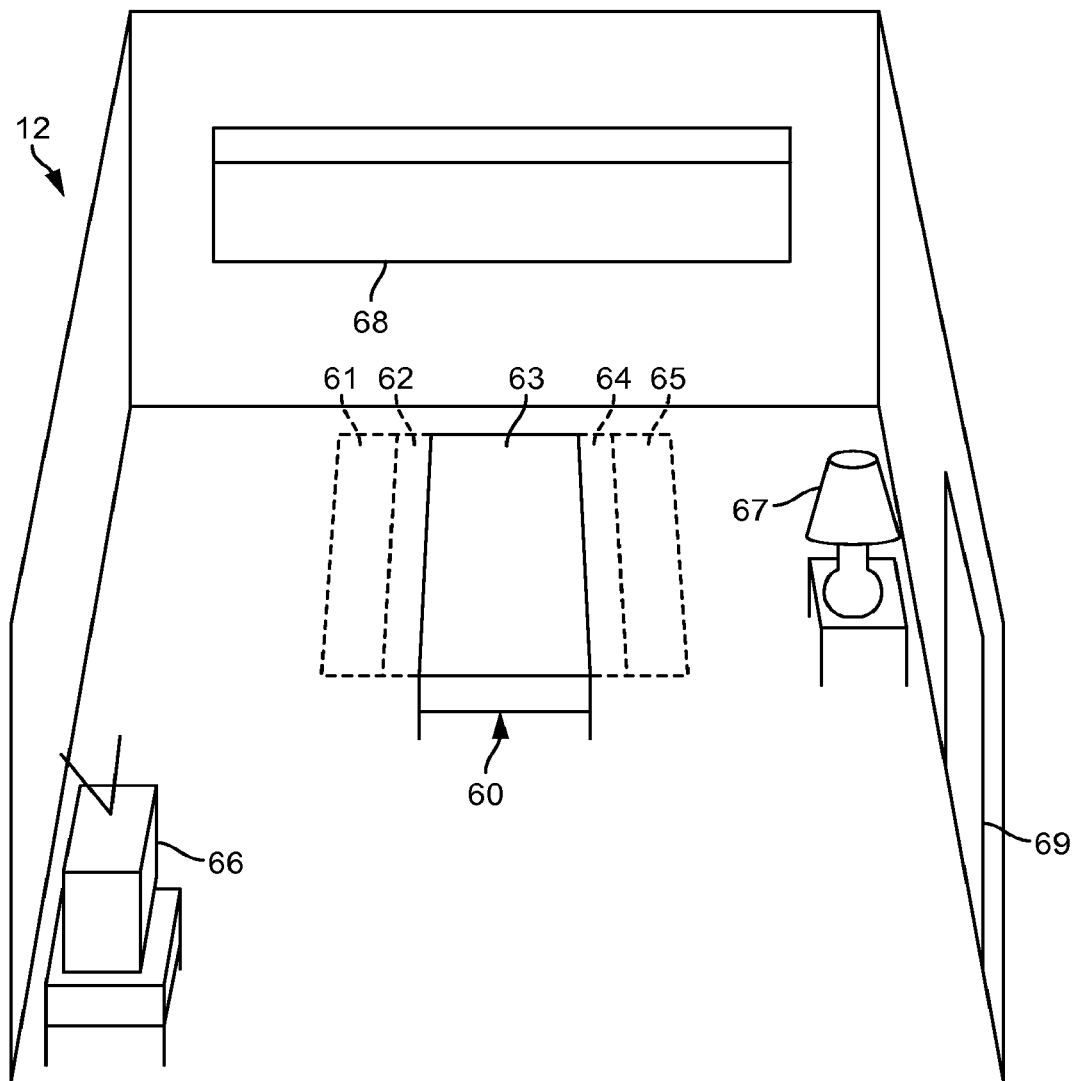
FIG. 4 is a schematic diagram of a patient area.

One or more zones can be defined 52 based on the received 51 user input. For example, one or more zones within and/or outside of a boundary designation can be defined by an algorithm. The one or more zones can correspond with areas of increased risk to a patient, such as areas adjacent to and/or over the side of the bed (e.g., as a virtual bedrail). In some embodiments, the one or more zones correspond to areas where patient motion is expected and/or where patient motion can be indicative of dangerous or otherwise unwanted activity. In some cases, a plurality of zones can be defined 52 to cover the bed and/or extend along the bed or other patient area. Various rules can be used by an algorithm of a monitoring system to define 52 the one or more zones. For example, a longitudinal dimension of a zone can be defined 52 as extending parallel with the longitudinal dimension of a bed as indicated by the received 51 input. The zones can be defined 52 in dimensions of pixels. A width dimension of a zone can be defined as extending outward from the boundary designations (e.g., away from the bed) for a predetermined number of pixels. The predetermined number of pixels may correspond with a distance, such as twelve inches. FIG. 4 shows five zones that can be manually or automatically defined 52 based on user input. Specifically, a left outer zone 61, a left inner zone 62, a center zone 63, and right inner zone 64, and a right outer zone 65 are defined 52 along the bed 60.

The method of FIG. 3 further includes monitoring 53 the defined 52 zones. Motion in the center zone 63 may be indicative of normal patient movement, but motion detected within either of the left inner zone 62 or the right inner zone 64 can indicate that the patient is at least partially off the bed 60 and at risk of falling. Different rules for monitoring 53 can be applied for the inner zones 62 and 64 as compared to the outer zones 61 and 65. For example, the inner zones 62 and 64, where the patient is most likely to fall, can be monitored 53 to trigger a fall alert or other indication. The outer zones 61 and 65, which are positioned to intercept visitors, can be monitored 53 to temporarily disarm the monitoring system to prevent a visitor from erroneously triggering the fall alert or other indication.

Monitoring 53 of the zones can allow particular discrimination algorithms to be run using the pixels of the zones to identify patterns or other indication of a patient event. For example, an algorithm can compare pixel characteristics of a zone between sequential frames to determine whether the pixel characteristic of the zone changed, the change indicative of patient movement. While monitoring 53 algorithms will be further described herein, it may be useful to describe pixel luminance and other pixel characteristics used in monitoring 53.

Each pixel of a frame can be associated with luminance and other optical characteristics. The luminance characterizes the intensity of the light associated with the pixel. Luminance can be particularly useful because luminance can be measured in dark environments, such as at night. Luminance can be used for motion detection by identifying changes in the luminance of a zone over time. The luminance of a zone may change over time (e.g., between sequential frames) because the reflectance of the surfaces within the zone can change due to movement of the surfaces. For example, a patient's arm can move into a zone, thereby changing the luminance of the zone to be darker or lighter. Comparisons between some luminance-based metric of a zone between frames can determine whether the change in luminance is indicative of patient movement within the zone. For example, the change in luminance may be compared to a threshold, the threshold distinguishing small changes in luminance unlikely to be associated with patient movement (e.g., noise) and larger changes in luminance likely to be from patient movement. However, changes in illumination of the patient area can cause larger changes in luminance of the zone. Such a large change in luminance in the zone can be misidentified as patient motion or other event, potentially triggering a false alarm.

Referring to FIG. 4, the patient area 12 includes several sources of light that can change the luminance of the zones 61-65 and frustrate accurate detection of patient motion and/or cause erroneous detections. For example, turning the television 66 on and off can change the illumination of the patient area 12. Furthermore, the television 66 can cause light flicker within the patient area 12 as the screen changes between bright and dark scenes, which is referred to herein as flicker noise. The lamp 67 or other lighting device can be turned on and off to change the illumination of the patient area 12. The window 68 can allow outside light into the room. The amount of outside light coming through the window 68 can change due to clouds unpredictably blocking and unblocking direct sunlight. An outside light can come through the doorway 69 to change the illumination of the room. The outside light can be turned on and off and/or the doorway 69 can be obscured by the door opening/closing or a person moving through the doorway 69. A camera transitioning between day and night modes (e.g., between ambient light and infrared operation) can abruptly change the perceived illumination of the patient area 12. Such changes in illumination can cause changes in the luminance of pixels within the zones 61-65 and cause erroneous detections of motion and false alarms. Various embodiments of the present disclosure are directed to systems and methods for accounting for such changes in illumination to limit erroneous detections and false alarms. Such methods are further described in connection with FIGS. 5 and 6.

Figure 5:
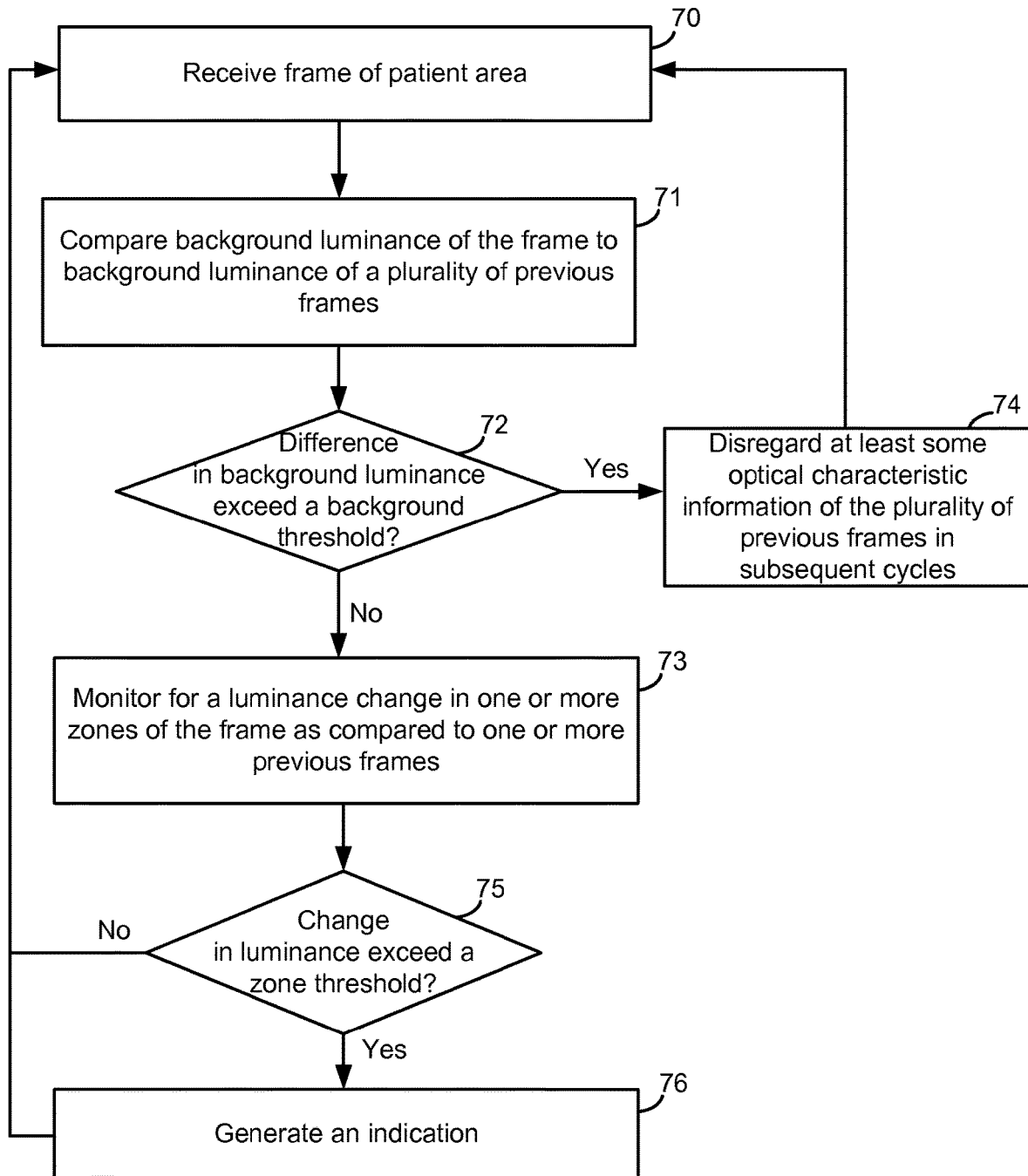
FIG. 5 is a flow chart of a method for monitoring a patient and accounting for changes in illumination.

FIG. 5 shows a flow chart of a method for monitoring a patient while accounting for changes in illumination of the patient area. The method can be implemented in a monitoring system (e.g., as program instructions) as referenced herein. Some embodiments of the method may be preceded by an initial setup procedure, such as that of FIG. 3. In any case, the method of FIG. 5 includes the reception 70 of a frame. The frame can be part of a chronological series of frames generated by the camera and transmitted to a computing system in sequence, wherein the steps of the method are performed for the reception 70 of each respective frame of the chronological series. Accordingly, the method steps of FIG. 5 represent one iteration of a cycle, the cycle being repeated for each frame received 70.

The method includes comparing 71 background luminance of the received 70 frame to background luminance of a plurality of previously received 70 frames. The background luminance of a frame can be based on an aggregate measure of the respective luminance values of most or all of the pixels of the frame. As such, the background luminance can represent the general illumination of the patient area and the overall luminance of the frame. In some cases, the background luminance can be calculated only from pixels of a specific selection of the patient area that is not occupied by the patient or otherwise part of a zone monitored for movement (e.g., an area of the floor and/or wall). While the background luminance can be calculated according to various techniques, some specific techniques for calculating background luminance are elsewhere discussed in the present disclosure.

The comparison 71 of the background luminance of the frame to the background luminance of the plurality of previous frames can include determining a difference between the background luminance of the current frame (i.e. the frame received 70 in the current iteration of the method cycle) and the background luminance of a plurality of frames previously received 70 in previous cycles (e.g., five frames of the five most recently completed cycles). The background luminance of the plurality of frames can be aggregated into a single value, such as an aggregate background luminance of the plurality of frames, to which the background luminance of the current frame can be compared 71. For example, the aggregate background luminance of the plurality of frames can be the average of the background luminance of each of the plurality of previous frames. The use of the plurality of previous frames can function as a moving average of the background luminance over time, to which the background luminance of each current frame is compared 71. The comparison 71 can include determining a difference between the background luminance of the frame and the background luminance of the plurality of previous frames. The difference can be determined by subtraction and then optionally taking the absolute value of the result. While the comparing 71 step states that the background luminance of the frame is compared 71 to the background luminance of a plurality of previous frames, in some other embodiments the comparing 71 steps concern comparing 71 the background luminance of the frame to background luminance of one of the plurality of previous frames.

Based on the comparison 71, the method can include determining whether the difference in background luminance between the current frame and the background luminance of the plurality of previous frames exceeds 72 a background threshold. The background threshold can be set to distinguish between changes in background luminance due to motion and larger changes in background illumination due to a change in the illumination of the room (e.g., due to television noise flicker, a light, and/or the sun). The background threshold can be set along any luminance-based metric. The background threshold can be a threshold amount. The threshold amount can be a predetermined amount (e.g., set by a user or a factory setting). A user can set the threshold based on a risk assessment. A particular example value for the background threshold is discussed elsewhere herein or based on a history of false detections. The threshold amount can be a dynamic threshold amount. For example, the dynamic threshold amount can be based on the current background luminance (e.g., 10% of current background luminance), such that the threshold is smaller in darker environments and larger in brighter environments. The dynamic threshold amount can be based on a statistic of the background luminance, such as a percentage of the standard deviation of the luminance of the pixels of the current frame or a plurality of previous frames. The dynamic threshold can be based on the relative amount of infrared content and non-infrared content of the background luminance. In some cases, multiple changes in background luminance over a plurality of frames that do not exceed the threshold can cause the threshold to be automatically raised If the difference in background luminance does not exceed 72 the background threshold, then the method can continue with monitoring 73 for a luminance change in one or more zones of the frame as compared to one or more previous frames. As discussed herein, motion and other events can be detected by comparing some luminance-based metric of a particular zone between a current and one or more prior frames to determine whether the value of the metric changed. Accordingly, the method can include determining whether a change in luminance of a zone exceeds 75 a zone threshold. The zone threshold can represent the difference in luminance between insubstantial changes due to low levels of noise and larger changes due to motion or other important events.

While changes in luminance can be identified by directly comparing zone luminance values from consecutive frames, changes in luminance can be determined by additional or alternative techniques. For example, another luminance-based metric is the number of edges within a zone. Edges can be detected by analyzing the contrast in luminance between neighboring pixels. High contrast indicates an edge while low contrast indicates the lack of an edge. Summing the edges detected within a zone can be useful in motion detection because the number of edges within a zone change from one frame to the next if motion is occurring within the zone. As such, monitoring 73 for a luminance change can include determining whether a change in the number of edges detected in a zone between two frames exceeds 75 a zone threshold.

If the zone threshold is exceeded 75, then an indication can be generated 76, such as a fall alarm and/or a changing of a patient state. The cycle can then be repeated with the reception 70 of the next frame of the chronological series. However, returning to the step of determining whether the difference in background luminance between the current frame and the background luminance of the plurality of previous frames exceeds 72 the background threshold, various steps can be taken if the background threshold is exceeded 72. In some cases, optical characteristic information (e.g., luminance values, color information, chrominance) of the plurality of previous frames can be disregarded 74 in subsequent iterations of the method cycle if the background threshold is exceeded 72. Disregarding 74 can include erasing luminance and/or other information from memory. In some embodiments, disregarding 74 may include not referencing the optical characteristic information of the plurality of previous frames in subsequent iterations of the cycle. Luminance values and/or other information of the plurality of previous frames may otherwise be referenced in the comparison 71 step and the monitoring 73 step in subsequent iterations of the cycle, yet this information will be disregarded 74 because the background threshold being exceeded 72 indicates that subsequent changes in luminance are likely due to the changes in environmental illumination and not motion within a zone. Accordingly, the optical information of the previous frames can be disregarded 74 so that the steps of the method that rely on the optical information of one or more previous frames (e.g., luminance background comparison 71 and zone monitoring 73) can refer to optical information that is more likely to reflect the current illumination conditions of the patient area. In some embodiments, all optical information of the plurality of previous frames can be disregarded 74. In some other embodiments, only some of the optical information of the plurality of previous frames may be disregarded 74, such as luminance, chrominance, and/or edge counts.

If the background threshold is exceeded 72, subsequent cycles of the method can refer to the background and zone luminance of the current frame (i.e. the frame for which the background threshold being exceeded 72 was detected), but not luminance values of frames preceding the current frame. In the subsequent cycles, the current frame will become a previous frame and may be referenced as a previous frame (e.g., in the comparison 71 and monitoring steps 73). Moreover, more frames subsequently received 70 can be referenced as previous frames for comparing past and current luminance until the background threshold is again exceeded 72, at which point the luminance values and/or other optical information of the previous frames are disregarded 74. In embodiments where the zone threshold represents a change in the number of edges in a zone, or detection of motion is otherwise based on the number of edges in a zone, the edge information can be disregarded 74 if the background threshold is exceeded 72. Other types of information used to detect motion can be disregarded 74 for the plurality of previous frames if the background threshold is exceeded 72.

The current frame, as the term is used herein, refers to the frame most recently received and for which the computing system is processing to detect motion, a change in background luminance, and/or another event. A previous frame, as the term is used herein, refers to a frame that was received previous to the current frame and represents a time that precedes the time represented by the current frame. The current frame can become a previous frame when the next frame (i.e. the new current frame) is received and monitoring based on the next frame begins, where the next frame becomes the current frame. If luminance information of the plurality of previous frames is disregarded 74, the luminance information of the current frame is not likewise disregarded 74 even though the current frame becomes a previous frame in the next cycle. Rather, disregarding 74 the luminance information of the plurality of previous frames refers to those frames which were previous frames at the time of the disregarding 74 step.

Figure 6:
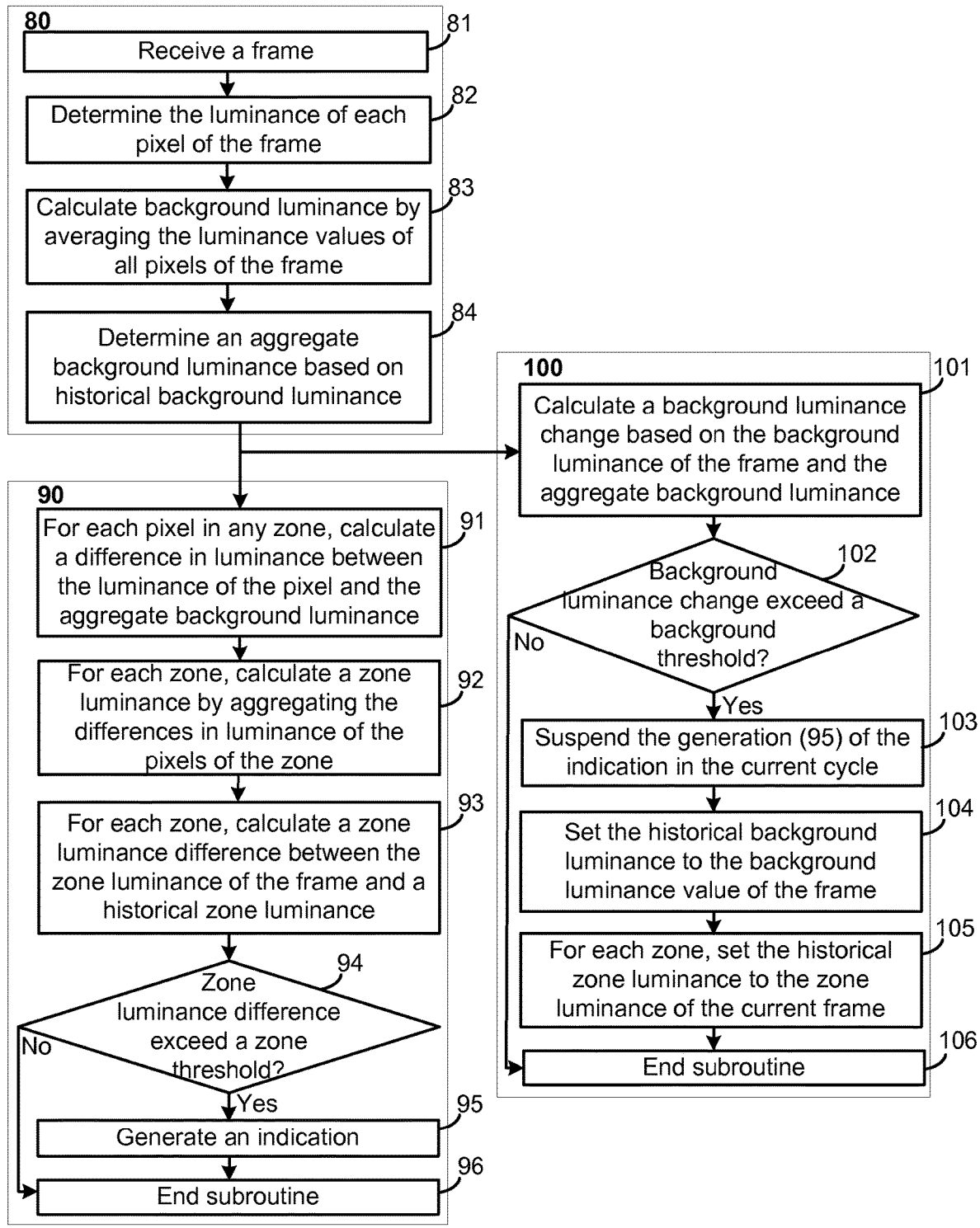
FIG. 6 is another flow chart of a method for monitoring a patient and accounting for environmental illumination changes.

FIG. 6 shows a flow chart of a method for monitoring a patient while accounting for changes in illumination of the patient area. Some embodiments of the method of FIG. 6 can also correspond to the flowchart of the method of FIG. 5 and/or other embodiments referenced herein. The method of FIG. 6 can be implemented in a monitoring system (e.g., as program instructions) as referenced herein. It is noted that the flowchart of FIG. 6 contains three subroutines that can each be performed as different parts of a cycle, each iteration of the cycle based on the reception 81 of a frame from a camera. Specifically, the method includes a background luminance subroutine 80 that determines at least one measure of the background luminance of the frame. The method further includes a zone detection subroutine 90 that detects movement or other conditions within one or more zones defined in the frame. The method further includes an environmental illumination correction subroutine 100. The subroutines can run concurrently or consecutively in various orders, however the background luminance subroutine 80 is typically completed before some or all of the steps of the other two subroutines are started as the background luminance subroutine 80 provides information to the other two subroutines.

The background luminance subroutine 80 includes receiving 81 a frame, which can occur in any manner referenced herein (e.g., the frame generated by a camera and part of a chronological series of frames). The background luminance subroutine 80 further includes determining 82 the luminance of each pixel of the frame. Luminance can be measured in various different ways. One technique for measuring luminance includes categorizing the intensity of each pixel along an 8-bit grayscale, where 0 can be the lowest possible intensity level (i.e. darkest) and 255 can be the highest possible intensity level (i.e. brightest). While other schemes for assessing the relative level of luminance of pixels are possible, this technique will be used herein as an exemplar.

The background luminance subroutine 80 further includes calculating 83 a background luminance value by averaging the luminance values of all pixels of the frame. The background luminance value is a measure of the luminance of the general pixels of the frame. Although the flowchart of FIG. 6 specifically identifies averaging of pixel luminance to determine the background luminance, various other aggregating techniques can be used to calculate a value representing the background luminance, such as median, mode, or standard deviation, among others.

The background luminance subroutine 80 can further include determining 84 an aggregate background luminance from historical background luminance. The historical background luminance can represent the background luminance or one or more previous frames, such as the five most recent previous frames. The aggregate background luminance can be a measure of the environmental luminance of multiple frames over time. In some cases, the aggregate background luminance is determined 84 from the background luminance of the current frame and a plurality of previous frames, the plurality of previous frames corresponding to the historical background luminance. The background luminance values of the plurality of previous frames and optionally the background luminance of the current frame can be averaged to determine 84 the aggregate background luminance. Other aggregating techniques can be used to represent the background luminance values over a plurality of frames, such as calculating the median, mode, or standard deviation of the background luminance values. Use of the aggregate background luminance instead of just a current background luminance can help smooth out the background luminance values and minimize transient changes in background luminance. However, it is noted that in some alternative versions of the method of FIG. 6, the aggregate background luminance may not be determined 84 and instead the background luminance is used in place for the subsequent steps of the method. Use of the aggregate background luminance (or alternatively the background luminance) is further described in connection with the zone detection subroutine 90 and the environmental illumination correction subroutine 100.

The zone detection subroutine 90 includes, for each pixel in any zone, calculating 91 a difference in luminance between the luminance of the pixel and the aggregate background luminance. Alternatively, the step may comprise calculating 91 a difference in luminance between the luminance of the pixel and the background luminance of the current frame. As discussed previously, each frame can have one or more zones which are monitored for motion or other event. The zones can be those of FIG. 4, for example. The difference in luminance can be calculated 91 by subtracting the luminance of the pixel from the aggregate background luminance or subtracting the aggregate background luminance from the luminance of the pixel, for example. In any case, the absolute value can be the taken in calculating 91 the difference between the luminance of the pixel and the aggregate background luminance such that positive and negative differences can be equally valued. For example, the aggregate background luminance may be 150 on the 8-bit grayscale, while a first pixel has a luminance of 140 and a second pixel has a luminance of 165. The calculated 91 difference associated with the first pixel can be 10 (assuming the absolute value is taken) and the calculated 91 difference associated with the second pixel can be 15.

The zone detection subroutine 90 can further include, for each zone of the frame, calculating 92 a zone luminance by aggregating the differences in luminance of the pixels of the zone. The zone luminance can represent a measure of the overall luminance of a zone. A plurality of zone luminance values can be calculated 92 for a plurality of zones such that each zone has a corresponding zone luminance. The aggregation can include determining the sum, average, median, mode, standard deviation, or other statistical metric from the calculated 91 difference of the luminance of the pixels of the zone with the aggregate background luminance. In the case of summing, and continuing with the example provided above, the first and the second pixels can be in the same zone, and as such can be summed to 25. Further difference values from the same zone can be aggregated to calculate the zone luminance.

The zone detection subroutine 90 can further include, for each zone of the frame, calculating 93 a luminance difference between the calculated 92 zone luminance of the zone and a historical zone luminance. The historical zone luminance can be the zone luminance of the same zone calculated 92 from the previous frame (e.g., calculated 92 in the most recently completed cycle of the method). The historical zone luminance can be based on the zone luminance of the same zone over a plurality of previous frames (e.g., the zone luminance values of the previous five frames averaged together). The calculated 93 zone luminance difference can represent the change in luminance of the zone between the previous frame and the current frame, which can be indicative of patient movement within the zone. As discussed previously, the calculated 93 zone difference can concern a change in the number of edges identified in a zone. The zone luminance difference can be compared to a zone threshold to determine whether the zone luminance difference exceeds the zone threshold. The zone threshold can represent the difference between minor changes in luminance due to noise and larger changes in luminance due to movement. The zone threshold can be set for each zone and may be the same or different for the different zones. The zone threshold may be a predetermined amount. For example, the zone threshold may be 2 on the 8-bit grayscale previously described.

If the zone threshold is exceeded 94, then the zone detection subroutine 90 can generate 95 an indication with a user interface. The indication may comprise designating the zone as active, representing a notification of an event on a screen, raising a patient fall state risk, and/or issuing an alert (e.g., an alarm to summon intervention). The zone detection subroutine 90 can end 96 with the generation 95 of the indication or if the zone threshold is not exceeded 94. It is noted that the generation 95 of the indication of the patient risk may be suspended by the environmental illumination correction subroutine 100 as further discussed herein.

The environmental illumination correction subroutine 100 can account for changes in illumination between frames. In doing so, the environmental illumination correction subroutine 100 can prevent erroneous event detections and false alarms by disregarding detections possibly caused by the change in illumination and can further reset various detection values to facilitate the quick recovery of the detection algorithm for subsequent cycles.

The environmental illumination correction subroutine 100 can include calculating 101 a background luminance change based on the background luminance of the current frame and the aggregate background luminance. The change can be a difference between the background luminance of the current frame and the aggregate background luminance. The change can be calculated 101 by subtracting the background luminance of the current frame from the aggregate background luminance or subtracting the aggregate background luminance from the background luminance of the current frame, for example. In any case, the absolute value can be the taken in calculating 101 the change such that a comparable difference can be assured. The calculated 101 difference can be compared to a background threshold to determine whether the background luminance change exceeds 102 the background threshold. The background threshold can represent the difference between changes in illumination due to patient motion and larger changes in illumination likely to trigger erroneous patient event detection. Continuing with the above example, the background threshold may be 10 on the 8-bit grayscale previously described. It is noted that the inventors of the subject matter of this disclosure have discovered that a threshold of about 10 on an 8-bit grayscale can be particularly effective, in some implementations, at distinguishing between luminance changes associated with patient motion and luminance changes associated with changes in environmental illumination.

Several steps can be taken in response to the background luminance change exceeding 102 the background threshold. In some cases, the generation 95 of indications based on the zone threshold being exceeded 94 in the current cycle can be suspended 103. In some cases, the zone detection subroutine 90 may be automatically ended 96 (regardless of whether the zone threshold is or will be exceeded 94) for the current cycle if the background threshold is exceeded 102. It may be appropriate to disregard the zone threshold being exceeded 94 because detections of motion or other events may be the result of the environmental illumination change and not actual motion. If the patient is indeed moving, such motion can still be detected in the next cycle as the algorithm recovers from the environmental illumination change.

The environmental illumination correction subroutine 100 can include setting 104 the historical background luminance to the background luminance of the current frame. As discussed previously, the aggregate background luminance can be determined 84 from the historical background luminance, which itself can be based on the background luminance of a plurality of previous frames. However, the luminance of the previous frames may deviate sharply from the luminance of the current frame and some number of subsequent frames if the environmental illumination of the patient area has changed. Accordingly, the method can include setting the historical background luminance to the background luminance of the current frame. It is noted that the historical background luminance may preferably be calculated from a plurality of consecutive frames (e.g., three or five frames) to provide a smoothing function, however it may be more important to forgo such smoothing when a environmental change in illumination is detected. Accordingly, if the historical background luminance is set 104 to a single frame (i.e. the current frame) instead of being based on the plurality of previous frames, then in the next cycle the aggregate background luminance may be based on the single frame or two frames (e.g., if the aggregate background luminance is determined 84 based on the background luminance of the current frame and the historical background luminance). The number of frames used to calculate the historical background luminance can be built back up over several cycles to restore the smoothing function as the background luminance is calculated 83 for each frame received 81.

For each zone, the historical zone luminance associated with the zone can be set 105 to the zone luminance of the current frame. The zone luminance can be calculated 92 as part of the zone detection subroutine 90 or can be calculated separately (e.g., in case the zone detection subroutine 90 is not completed due to the background threshold being exceeded 102). Setting 105 the historical zone luminance of each zone to a respective zone luminance of the current frame can help the zone detection subroutine 90 to quickly adjust to the new illumination of the patient area in the next cycle. In some cases, the historical zone luminance of each zone may be based on a plurality of previous frames (e.g., a moving zone luminance average of consecutive frames), but if the environmental illumination of the patient area has changed, then the zone luminance of the previous frames are likely to be misleading for detecting changes in zone luminance due to motion. Accordingly, the method can include setting 105 the zone luminance for each zone to a respective zone luminance of the current frame that reflects the environmental change in illumination. The zone detection subroutine 90 of the following cycle will then have a more relevant historical zone luminance value with which to calculate 93 the zone luminance difference in determining whether a change in luminance of a zone is indicative of motion or other event. Although each of the suspending 103, setting 104 the historical background luminance, and setting 105 the historical zone luminance are each shown in the environmental illumination correction subroutine 100, various embodiments can selectively include or omit these and other steps triggered in response to the background threshold being exceeded 102. A new cycle may begin when the environmental illumination correction subroutine 100 ends 106 and the next frame is received 81.

In addition to, or as an alternative to, setting 105 the historical zone luminance, zone luminance information of a plurality of previous frames can be disregarded or otherwise dampened based on the background threshold being exceeded 102. The luminance information may concern calculated 92 zone luminance values for each zone over the plurality of previous frames. Dampening luminance information is discussed elsewhere herein, and can include erasing the luminance information for the zones of the plurality of previous frames or applying a scalar (e.g., 0.8) to the data. Accordingly, in some cases, edge detection information from each of the zones can be erased or otherwise disregarded if the background threshold is exceeded 102.

The flowchart and block diagrams in the FIGS. of the present disclosure illustrate the architecture, functionality, and operation of some possible implementations of systems, methods, and computer program products according to various embodiments of the present disclosure. In this regard, each step in the flowchart or arrangement of blocks may represent a component, module, segment, or portion of code, which comprises one or more executable instructions for implementing the specified logical function(s). It should also be noted that, in some alternative implementations, the functions noted in the steps may occur out of the order noted in the FIGS. or as otherwise described. For example, two steps shown in succession may, in fact, be executed substantially concurrently, or the steps may sometimes be executed in the reverse order, depending upon the functionality involved.

It is noted that reception of a frame (e.g., by a computing system from a camera) does not necessarily mean reception of all of the data of the frame sufficient to reconstruct the entire frame. Rather, reception of the frame can include reception of representative data (e.g., luminance information) that allows for calculation of the background luminance and other values for performing the functions described herein.

While luminance has been used as an example optical characteristic herein for adjusting a detection algorithm, various other optical characteristics can be used in place of, or in addition to, luminance in any of the embodiments referenced herein. An optical characteristic can be measured based on the intensity or degree of content. An optical characteristic can include chrominance. Optical characteristics can include color content, or one or more particular components of color (e.g., red, green, blue, and/or other color). Color can be measured by any measure of color space. The term "luminance" can be replaced by "optical characteristic" in the method of FIG. 5 (or another any embodiment specifically directed to luminance). For example, various embodiments can concern a system for monitoring a patient in a patient area having one or more detection zones, the system comprising: a computing system configured to receive a chronological series of frames and perform the following steps based on the reception of each frame of the chronological series: calculate a background optical characteristic of the frame; for each zone of one or more zones of the frame, monitor for a optical characteristic change of the zone as compared to one or more frames of a plurality of frames that were previously received from the camera, the optical characteristic change indicative of patient motion in the zone; compare the background optical characteristic of the frame to an aggregate background optical characteristic, the aggregate background optical characteristic based on the plurality of frames; and if the comparison determines that the background optical characteristic changed relative to the aggregate background optical characteristic by more than a predetermined amount, set the aggregate background optical characteristic to the background optical characteristic of the frame and dampen optical characteristic of the plurality of frames in subsequent monitoring for the optical characteristic change in the one or more zones. The term "luminance" can be replaced by "color" in the method of FIG. 5 or another any embodiment. For example, various embodiments can concern a system for monitoring a patient in a patient area having one or more detection zones, the system comprising: a computing system configured to receive a chronological series of frames and perform the following steps based on the reception of each frame of the chronological series: calculate a background color of the frame; for each zone of one or more zones of the frame, monitor for a color change of the zone as compared to one or more frames of a plurality of frames that were previously received from the camera, the color change indicative of patient motion in the zone; compare the background color of the frame to an aggregate background color, the aggregate background color based on the plurality of frames; and if the comparison determines that the background color changed relative to the aggregate background color by more than a predetermined amount, set the aggregate background color to the background color of the frame and dampen color of the plurality of frames in subsequent monitoring for the color change in the one or more zones.

The techniques described in this disclosure, including those of FIGS. 1-6 and those attributed to a monitoring system, a computing system, a processor, and/or control circuitry, and/or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. A "computing system" as used herein refers to at least one of the foregoing logic circuitry as a processor, alone or in combination with other circuitry, such as memory or other physical medium for storing instructions, as needed to carry about specified functions (e.g., processor and memory having stored program instructions executable by the processor for detecting motion in one or more zones, detecting environmental illumination changes based on background luminance, and performing various steps in response to one or both of detecting motion and detecting environmental illumination change). The functions referenced herein and those functions of FIGS. 1-6, may be embodied as firmware, hardware, software or any combination thereof as part of a computing system specifically configured (e.g., with programming) to carry out those functions, such as in means for performing the functions referenced herein. The steps described herein may be performed by a single processing component or multiple processing components, the latter of which may be distributed amongst different coordinating devices. In this way, the computing system may be distributed between multiple devices, including part of a camera and part of a computer. In addition, any of the described units, modules, or components may be implemented together or separately as discrete but interoperable logic devices of a computing system. Depiction of different features as modules or units is intended to highlight different functional aspects and does not necessarily imply that such modules or units must be realized by separate hardware or software components and/or by a single device. Rather, functionality associated with one or more module or units, as part of a computing system, may be performed by separate hardware or software components, or integrated within common or separate hardware or software components of the computing system.

When implemented in software, the functionality ascribed to a computing system may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of the computing system. The instructions may be executed to support one or more aspects of the functionality described in this disclosure.

The particular embodiments described below are not intended to limit the scope of the present disclosure as it may be practiced in a variety of variations and environments without departing from the scope and intent of the invention. Thus, the present disclosure is not intended to be limited to the embodiments shown, but is to be accorded the widest scope consistent with the principles and features described herein. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for monitoring a patient in a patient area having one or more detection zones, the system comprising:
    a computing system that receives a chronological series of frames from a camera and performs the following steps based on the reception of each frame of the chronological series:
    calculate a current background luminance of a current frame;
    calculate an aggregate background luminance based on a respective background luminance for each of a plurality of previous frames of the chronological series;
    for each of one or more zones of the current frame, calculate a current number of edges within the zone;
    for each of the one or more zones of the current frame, detect patient motion based on a change between the current number of edges within the zone and a previous number of edges within a corresponding zone from one or more previous frames;
    compare the current background luminance of the current frame to an aggregate background luminance;
    in response to the current background luminance changing relative to the aggregate background luminance by more than a predetermined amount, disregard the detection of patient motion, set the current number of edges for each of the one or more zones as the previous number of edges for each of corresponding one or more zones from the one or more previous frames, and set the current background luminance as the aggregate background luminance in subsequent detection for patient motion; and in response to the current background luminance changing relative to the aggregate background luminance by less than the predetermined amount, generate an alert with a user interface based on the detection of patient motion.

2. The system of claim 1 further comprising the computing system configured to calculate the current number of edges by analyzing contrast in luminance values between neighboring pixels within the zone.

3. The system of claim 1 further comprising the computing system configured to detect patient motion according to distinctive rules for each of the one or more zones.

4. The system of claim 3 wherein the distinctive rules include a fall alert for given ones of the one or more zones corresponding to where a patient is likely to fall.

5. The system of claim 3 wherein the distinctive rules include disarming of patient motion detection in given ones of the one or more zones corresponding to visitors.

6. The system of claim 1 wherein the predetermined amount comprises a dynamic threshold amount that changes based on the current background luminance or a background luminance of at least one of the plurality of previous frames.

7. The system of claim 1 wherein the predetermined amount comprises a dynamic threshold amount that is smaller in darker environments and larger in brighter environments.

8. The system of claim 1 wherein the predetermined amount comprises a percentage of a standard deviation of the current background luminance or a background luminance of at least one of the plurality of previous frames.

9. The system of claim 1 wherein the predetermined amount is based on a relative amount of infrared content and non-infrared content of the current background luminance.

10. A system for monitoring a patient in a patient area having one or more detection zones, the system comprising:

a computing system that receives a chronological series of frames and performs the following steps based on the reception of each frame of the chronological series:

calculate a current background luminance of a current frame;

for each zone of one or more zones of the current frame, monitor for a change in a number of edges within the zone as compared to one or more frames of a plurality of frames that were previously received from a camera, the change in the number of edges indicative of patient motion in the zone of the current frame;

compare the current background luminance of the current frame to an aggregate background luminance; and in response to the comparison determining that the current background luminance changed relative to the aggregate background luminance by more than a predetermined amount, disregard change in a number of edges as being indicative of patient motion in the current frame, and monitor for changes in a number of edges for each zone of one or more zones of a next frame as compared to the current frame.

11. The system of claim 10 further comprising the computing system configured to calculate the current number of edges by analyzing contrast in luminance values between neighboring pixels within the zone.

12. The system of claim 10 further comprising the computing system configured to generate an alert in response to the monitoring step identifying the change in the number of edges.

13. The system of claim 10 further comprising the computing system configured to monitor for the zone luminance change according to distinctive rules for each of the one or more zones.

14. The system of claim 13 wherein the distinctive rules include a fall alert for given ones of the one or more zones corresponding to where a patient is likely to fall.

15. The system of claim 13 wherein the distinctive rules include disarming of patient motion detection in given ones of the one or more zones corresponding to visitors.

16. The system of claim 10 wherein the predetermined amount comprises a dynamic threshold amount that changes based on the current background luminance or a background luminance of at least one of the plurality of previous frames.

17. The system of claim 10 wherein the predetermined amount comprises a dynamic threshold amount that changes based on the current background luminance or a background luminance of at least one of the plurality of previous frames.

18. The system of claim 10 wherein the predetermined amount comprises a dynamic threshold amount that is smaller in darker environments and larger in brighter environments.

19. The system of claim 10 wherein the predetermined amount comprises a percentage of a standard deviation of the current background luminance or a background luminance of at least one of the plurality of previous frames.

20. A method for processing a chronological series of frames generated by a camera to monitor a patient in a patient area having one or more detection zones by performing the following steps based on the generation of each frame in the chronological series, each step performed at least in part by a computing system:

calculating a current background luminance of a current frame;

for each zone of one or more zones of the current frame, monitoring for a change in a number of edges within the zone as compared to one or more frames of a plurality of frames that were previously received from a camera, the change in the number of edges indicative of patient motion in the zone of the current frame;

comparing the current background luminance of the current frame to an aggregate background luminance; and in response to the comparison determining that the current background luminance changed relative to the aggregate background luminance by more than a threshold amount, disregarding change in a number of edges as being indicative of patient motion in the current frame, and monitoring for changes in a number of edges for each zone of one or more zones of a next frame as compared to the current frame.

\* \* \* \* \*